United States Patent [19]

Hamblen et al.

[11] 4,053,381
[45] Oct. 11, 1977

[54] DEVICE FOR DETERMINING IONIC ACTIVITY OF COMPONENTS OF LIQUID DROPS

[75] Inventors: David Philip Hamblen, Rochester; Clyde Pershing Glover, Pittsford; Sang Hyung Kim, Rochester, all of N.Y.

[73] Assignee: Eastman Kodak Company, Rochester, N.Y.

[21] Appl. No.: 687,725

[22] Filed: May 19, 1976

[51] Int. Cl.² .................. G01N 27/46; G01N 27/58
[52] U.S. Cl. ........................... 204/195 M; 204/195 R
[58] Field of Search ............... 204/195 R, 195 B, 1 T, 204/195 M; 23/253 R

[56] References Cited

U.S. PATENT DOCUMENTS

| 3,046,786 | 7/1962 | Tessem | 204/195 R |
|---|---|---|---|
| 3,474,022 | 10/1969 | Culpepper et al. | 204/195 R |
| 3,502,560 | 3/1970 | Wise | 204/195 |
| 3,575,834 | 4/1971 | Hoole et al. | 204/195 F |
| 3,598,713 | 8/1971 | Baum et al. | 204/195 L |
| 3,753,887 | 8/1973 | Kedem et al. | 204/195 M |
| 3,826,734 | 7/1974 | Godsey | 204/299 |
| 3,855,100 | 12/1974 | Haddad | 204/195 F |
| 3,856,649 | 12/1974 | Genshaw | 204/195 F |

FOREIGN PATENT DOCUMENTS

| 704,552 | 2/1954 | United Kingdom | 204/195 R |

*Primary Examiner*—G. L. Kaplan
*Attorney, Agent, or Firm*—Dana M. Schmidt

[57] ABSTRACT

A device and a method are disclosed for determining ion activity in liquids by the use of electrodes, particularly comprising an electrode mounting frame and transport means for promoting ionic migration between electrodes in the frame. Preferably, such electrodes are ion-selective electrodes.

33 Claims, 14 Drawing Figures

U.S. Patent  Oct. 11, 1977  Sheet 2 of 4  4,053,381
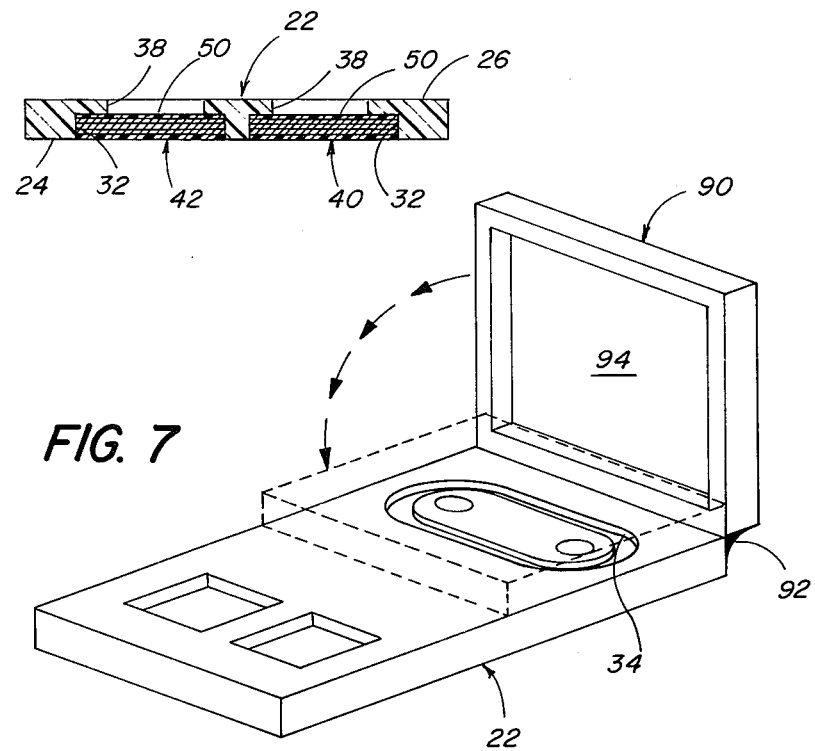
FIG. 3
FIG. 7
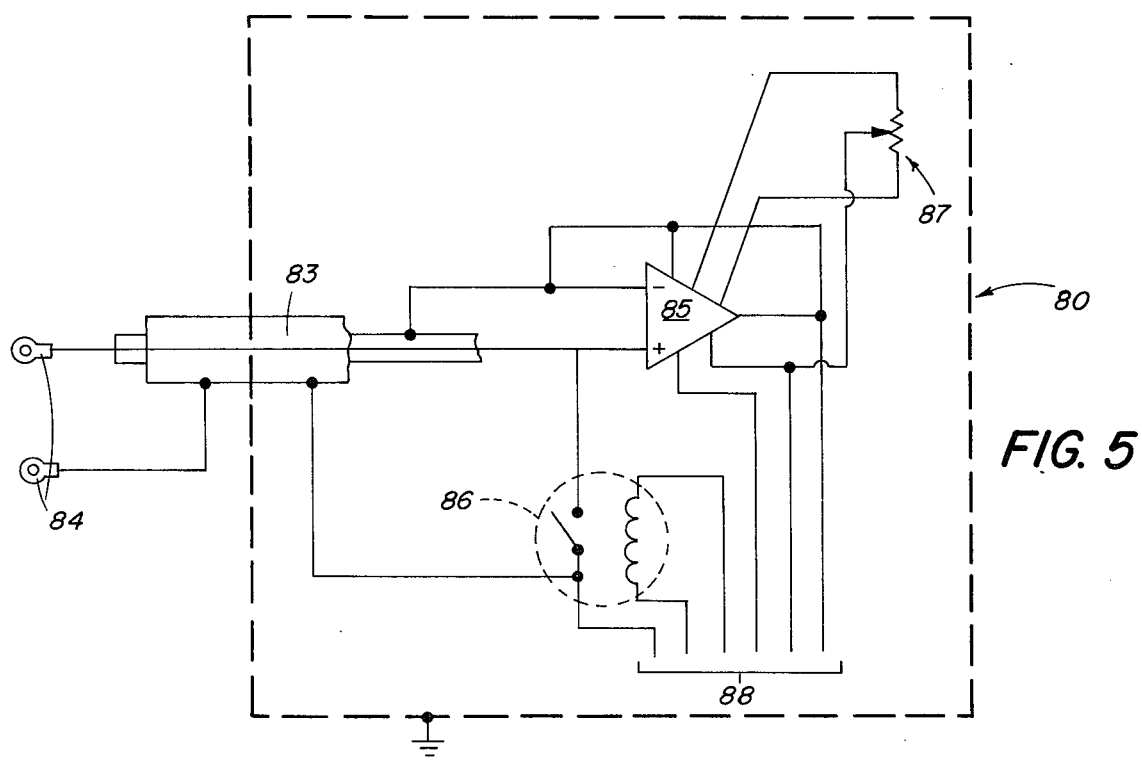
FIG. 5

DEVICE FOR DETERMINING IONIC ACTIVITY OF COMPONENTS OF LIQUID DROPS

BACKGROUND OF THE INVENTION

1. Field of the Invention

This invention relates to a device and a method for determining concentration of ionic liquid components contained in test samples, using electrically contacted substrates such as ion-selective electrodes. The device particularly concerns means for mounting electrodes so as to minimize errors in the readings obtained, and preferably is used in potentiometrically measuring ion activity in drops of biological fluids. Such measurments are used to measure the health of patients from which the fluids are taken, and can be ascertained either by a direct or a differential mode of measurement.

2. State of the Prior Art

The prior art is replete with a great variety of electrode types and structures for the measurement of various ions in solution. Typically, devices for obtaining such measurements include a reference electrode and an ion-selective electrode (hereafter termed ISE) which incorporates a reference half-cell, generally comprising a solution of known ion activity. When simultaneously immersed into the same body of solution to be analyzed, the reference electrode and the ISE constitute an electrochemical cell, across the electrodes of which a potential develops. This potential is proportional to the logarithm of the activity of the ions in the solution to which the ISE is sensitive. The foregoing relationship between the potential and the activity of the selected ion in solution is described by the well-known Nernst equation. An electrometric device, usually either a direct-reading circuit or a null-balance potentiometric circuit, is employed for measuring the potential between the electrodes.

Prior electrodes include barrel types, which have required large amounts of test solution into which they are immersed. U.S. Pat. Nos. 3,598,713; 3,502,560; 3,575,834 to Hoole issued Apr. 20, 1971; 3,753,887 to Kedem et al. issued Aug. 21, 1973 and U.S. Pat. No. 3,855,100 provide detailed descriptions of electrodes of this type. Such electrodes are not suitable for measuring drop-size amounts. Micro-amounts, if usable, would have a distinct advantage over large quantities, as the amounts of sample taken from the patient can be considerably reduced.

Yet another disadvantage of large, bulky electrodes such as the barrel type is their expense. Such devices do not lend themselves to the economy of mass production. A much desired improvement is an electrode whose mass-producible construction reduces its cost such that the electrode can be used once and disposed of, eliminating cleaning between tests and potential contamination.

Some miniaturization has been achieved by electrodes other than ion-selective electrodes and their supporting equipment. One example is the probe shown in British Patent Specification 1,318,815, wherein two electrodes are mounted spaced apart with a semipermeable matrix overlying the electrodes. However, there is no indication that these electrodes are to be used with drop-sized quantities of liquid or are disposable. Other miniaturized test elements have been developed, such as electrophoretic cells, wherein two electrodes are connected by a strip prewetted or precoated with an electrolyte to provide electrolytic connection to the electrodes when a drop of the test sample, such as blood serum, is applied to the strip. An example is shown in U.S. Pat. No. 3,826,734. However, the electrodes and mounting frame of such test elements are not designed for automated handling.

A solid state type of ion-selective electrode of greatly simplified construction is shown in U.S. Pat. No. 3,856,649 issued to Genshaw et al. on Dec. 24, 1974. Although the disclosure suggests that such ISE's could be constructed in sheet form, there is no teaching as to the manner in which the electrodes are useful or can be used in automated handling equipment. Specific problems of such automation are not dealt with.

Thin-layer chromatographic sheets, described hereinafter in connection with one embodiment of the invention, are of course, conventional and comprise a support coated with a layer such as silica gel mixed with a binder and a thickener to promote spreading of solvents. However, the test samples applied to such sheets are confined to a single spot or line, and separate test samples are deliberately segregated from each other.

U.S. Pat. No. 3,855,100 is an example of one type of salt bridge used in pH measurements.

RELATED APPLICATIONS

A recently developed ISE which is disposable and can be used with drop-sized test samples is shown in commonly owned U.S. Application Ser. No. 687,966, filed on May 19, 1977, by C. Battaglia et al, entitled "Ion Selective Electrode".

OBJECTS OF THE INVENTION

It is an object of the invention to provide an ISE test device and method which permits disposable electrodes to be used in high-volume automated processing machinery.

It is a related object of the invention to provide such a device and method which is insensitive to indiscriminate handling that is common in automated processing.

Yet another, related object of the invention is to provide a frame for the electrodes of such a device and method, which frame minimizes the size, permits mass reproduction, and thus reduces the cost of the device.

Other objects and advantages will become apparent upon reference to the following Summary of the Invention and Description of the Preferred Embodiments, when read in light of the attached drawings.

SUMMARY OF THE INVENTION

The invention concerns a device and a method for determining activity of ions in a liquid test solution of minimum size, and preferably, through the use of ISE's.

More specifically, there is provided a device useful for determining the activity of ions in a liquid solution, comprising a frame capable of being processed by automatic handling devices, two solid electrodes mounted with respect to the frame, each comprising a first operative layer coated over at least one other operative layer, the layers terminating at edges, means for providing ionic flow between said electrodes by application of one or more liquid drops, and at each electrode, means for restraining the liquid from contacting the edge of the other layer while in fluid contact with a portion of the liquid in contact with the edge of the first layer.

To determine activity, each of a pair of electrodes is contacted with a drop of liquid via a transport element such that ionic flow occurs between the electrodes, electrical contact is made with the electrodes, and the electrical potentials at the interfaces between the drops of liquid and the electrodes are compared.

BRIEF DESCRIPTION OF THE DRAWINGS

FIG. 3 is a sectional view taken generally along the plane designated as III-III in FIG. 1;

FIG. 5 is a schematic of the circuit of the electrometer shown in FIG. 1;

FIG. 7 is an isometric view similar to FIG. 1 but illustrating a modification thereof;

DESCRIPTION OF THE PREFERRED EMBODIMENTS

Although the invention as hereinafter described is directed to a device and a method for potentiometrically determining ion activity through the use of ISE's, such device and method are not so limited and can be applied to other electrical tests of a liquid solution using the appropriate electrodes or substrates, particularly when the amount of test liquid is no more than a drop, i.e., up to about 100 μl.

The terms "upper", "lower" and the like as used herein refer to orientations during actual use of the device.

The invention thus concerns a device particularly adapted for processing by automated handling devices, such as a mounting frame for two solid electrodes, each comprising a first operative layer coated over at least one other operative layer, and means for providing ionic flow between the electrodes. As used herein, "operative" means effective to assist in the potentiometric determination of the activity of the ion of choice.

It has been found that automated tests using ionselective electrodes are facilitated if the electrodes are transferred by automated handling devices between stations, such as from the drop-application station to the electrometer station, with the result that the electrodes experience considerable agitation. Such agitation is of little consequence to the device per se, but it causes substantial dynamic instability to the drops of test samples deposited on the device. Such instability is a particular problem when, as in the preferred embodiments, the electrode layers into which the ion of choice is to penetrate, terminate at edges susceptable to short-circuiting if the liquid flows into contact with those edges. One aspect of the invention is the provision of a device appropriately constructed to prevent such short-circuiting.

Figure 1:
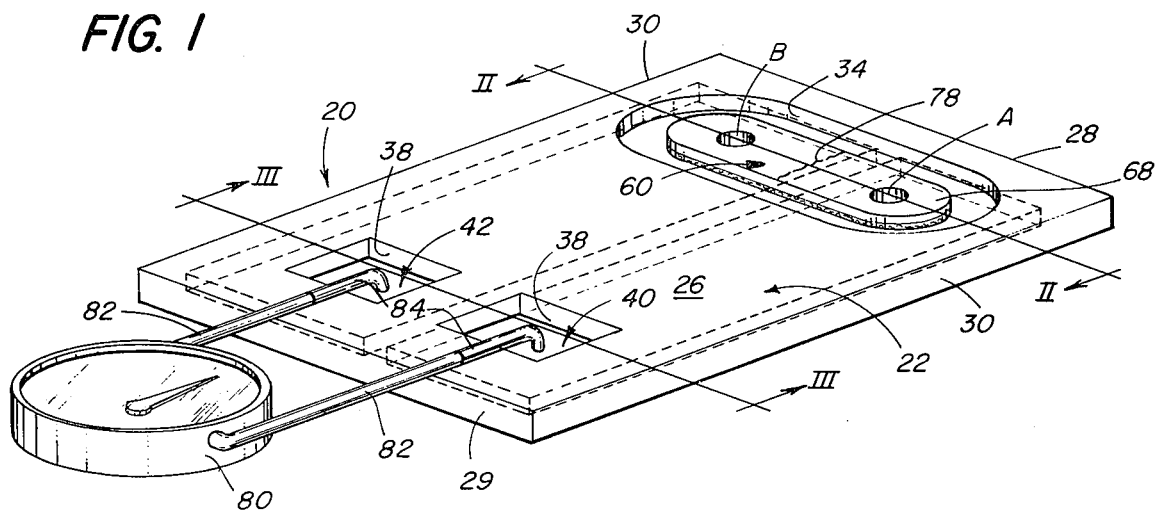
FIG. 1 is an isometric view of apparatus constructed in accordance with the invention.

Turning now to FIG. 1 there is illustrated a device 20 which comprises a mounting frame 22, two solid substrates 40 and 42 which are preferably electrodes (shown partially in phantom) mounted in the frame electrically isolated from each other, and transport means 60 for promoting ionic migration between liquid drops deposited on the electrodes. An electrometer 80 connected by wires 82 and probes 84 to the electrodes through appropriate apertures in frame 22 permits comparison of potentials.

THE MOUNTING FRAME

Figure 2:
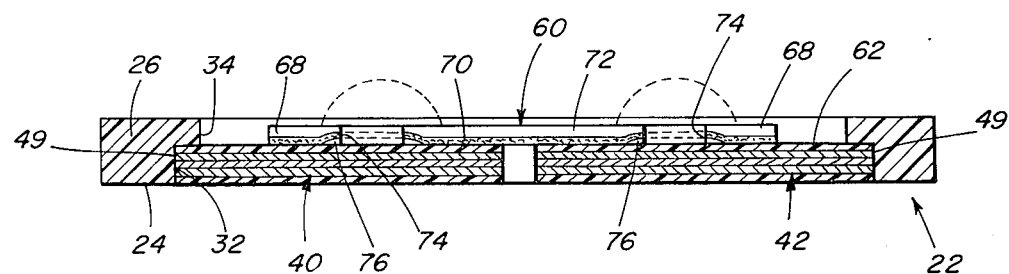
FIG. 2 is a sectional view taken generally along the plane designated as II-II in FIG. 1.

The frame 22, as best seen in FIGS. 1 and 2, comprises a generally planar body having opposed surfaces 24 and 26, ends 28 and 29, and edges 30. To hold the electrodes in proper relation, at least one groove or cavity 32 (FIG. 2) is formed in surface 24 of a shape and size to mate with electrodes 40 and 42, described hereinafter. Preferably, a pair of grooves are formed, FIG. 3. A single cavity can be used if the electrodes are electrically isolated by means other than the frame structure. Alternatively, groove 32 can be eliminated and the electrodes 40 and 42 can be secured directly to surface 24 by means such as adhesive. If a pair of grooves are used, they extend generally parallel to each other. As used herein, "cavity" means a space within a body which is either partially or completely enclosed by the body.

To permit access to the electrodes held by the frame, by both the liquid solutions and electrometer probes, access means are provided in the frame 22. Specifically, adjacent to end 28 is a transport passageway formed by a groove 34 in surface 26, which can be roughly elliptical in configuration. Groove 34 connects directly with grooves 32 by opening into the grooves.

A pair of additional apertures 38 are provided in surface 26 to provide electrical access to the electrodes 40 and 42, as best seen in FIG. 3. These apertures are formed adjacent end 29 and are used to permit contact of the probes 84 to the electrodes.

The frame 22 can be transparent or opaque and can be formed from a variety of materials provided they are electrically nonconductive. Molded plastics are highly preferred, and typical examples include acrylonitrilebutadiene-styrene copolymers, polyethylene, styrenes such as polystyrene, and nylons such as "Nylon 6" manufactured by duPont. A convenient size for the entire frame can be 2 to 3 cm. square, and 0.13 cm. thick.

It will be appreciated that the advantage of using grooves 32 and 34 is that the electrodes 40 and 42, and the transport means 60, are thereby recessed into the frame, so that a plurality of these devices can be stacked like slides and dispensed one at a time. In this fashion, the frame, electrodes and transport element are readily suited to high-speed, automated processing.

THE ELECTRODES

For the potentiometric measurements disclosed herein, the electrodes preferably include an ion-selective electrode and an external reference electrode, for a direct mode of determining potentials, or two ion-selective electrodes for a differential measurment comparing the ion activity of an unknown sample with that of a similar sample of known ion concentration. In either case, the electrode comprises first operative layer such as a membrane selectively permeable to the ion of choice, shown as layer 44 in FIG. 4, coated over at least one other operative layer.

Any layered type of electrode can be used in this invention. For ease in manufacturing, it is preferred that the layers be coated in an approximately planar format, rather than wire form, and in this format the edges of the layers are generally exposed and subject to short circuiting if sample migrates over such edges. As one example, the electrodes described and claimed in the aforesaid Battaglia application can be used.

Figure 4:
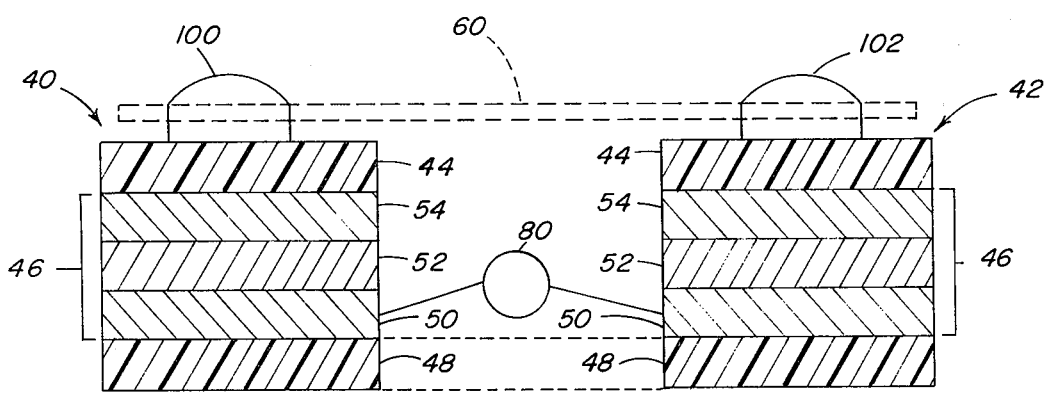
FIG. 4 is a schematic view similar to FIG. 2 which further illustrates the electrodes of the apparatus.

FIG. 4 is a schematic illustration of a highly preferred example of such an approximately planar format.

The electrodes 40 and 42 are shown as being identical, due to the differential mode of measurement which is made by electrometer 80 when a test drop 100 is applied to one and a reference drop 102 having a known concentration of ions is applied to the other. The thickness of the layers of the electrodes has been greatly exaggerated, for clarity. In actual practice, the entire electrodes are generally no greater than 0.20 mm. in thickness. Both electrodes then form in layered array operative layers comprising the ion-selective membrane 44, coated over an internal reference element 46 and a support 48, all of which are solid layers preferably in a dried condition. Although the layers are generally referred to as being "coated" one over another, it should be understood that the term "coating" is meant to include laminating or otherwise depositing the various strata one over another by any technique. It is apparent that the layers have exposed edges 49, FIG. 2.

The support 48 can be any material capable of bearing directly, or indirectly, through an adhesion-improving layer, the other layers. Thus, the support may comprise ceramic, wood, glass, metal, paper or cast, extruded or molded plastic or polymeric materials, etc. The composition of the support is relatively unimportant so long as it is capable of carrying the overlying electrode components and it is inert; i.e., it does not interfere with the indicating potentials observed as, for example, by reacting with one of the overlying materials in an uncontrolled fashion. In the case of porous materials such as wood, paper or ceramics, it may be desirable to seal the pores before applying the overlying electrode components.

In one preferred embodiment, a common support is used for both electrodes. In such a construction, shown in phantom in FIG. 4, a further requirement is that there be no electrical conduction between the electrodes through the support. Both electrodes can be coated as a single element on the common support, after which electrical separation is achieved by skiving a groove between the electrodes.

The reference element 46 is one which exhibits a fixed reference potential against which the potential occurring at the interface between the whole electrode and the solution under test is measured. The internal reference electrode may comprise several operative layers such as a metal layer 50 in contact with layer 52 of an insoluble salt of the metal which is in turn in contact with a layer 54 comprising an electrolyte, i.e., a solution containing the anion of the salt. A highly preferred embodiment of the element 46 utilizes the well-known Ag/Ag$_n$X (wherein X = S$^=$, Cl$^-$, Br$^-$ or I$^-$ and $n=1$ or 2) interface to establish a portion of the internal reference potential. In such a case, layer 50 is silver and layer 52 is Ag$_n$X. Electrodes of this type are well-known in the art and can be prepared using a number of well-known techniques which include, by way of example, dipping a layer of silver into a solution of molten silver halide. According to a preferred embodiment, the silver-silver halide half-cell is produced by vacuum-depositing silver onto a suitable support of the type described above, preferably an insulating film, and then chemically converting a surface stratum of the silver layer to silver halide. Other metals can also be used as layer 50. Although it is possible to obtain the metal-metal salt interface with any ratio of metal layer to salt layer thickness, in a preferred embodiment which assures a sufficiently dense layer of metal salt it is preferred that the insoluble metal salt layer have a thickness equal to at least 10% of the overall thickness of the metal layer.

As shown in FIG. 3, only layer 50 is exposed by apertures 40 and 42, as it is only this metal layer which must contact the probes 84, FIG. 5.

The second portion of the internal reference electrode comprises the electrolyte solution layer 54, FIG. 4, in contact with the metal salt layer 52. Preferably, the electrolyte solution is a dried hydrophilic layer and comprises a hydrophilic binder and a suitable ionic salt. Preferably, this salt comprises as the cation the ion of choice to be tested in drop 100 and, as the anion, the X that constitutes the salt of layer 52. The binder for the reference solution may comprise any hydrophilic material suitable for the formation of continuous coherent, cohesive layers compatible with the salt of the electrolyte layer and, if formed by coating, a solvent system for both the ionic salt and the polymeric binder. Useful materials of this type are hydrophilic natural and synthetic polymeric materials such as polyvinyl alcohol, gelatin, agarose, deionized gelatin, polyacrylamide, polyvinyl pyrrolidine, hydroxyethyl acrylate, hydroxyethyl methacrylate, etc.

With regard to the ionic salt of layer 54, if electrodes 40 and 42 are designed to determine the concentration of potassium, and layer 52 is AgCl, then the salt preferably is KCl. For sodium ion determinations in a similar configuration, sodium chloride would be preferred, etc. In the case of the analyte being the chloride anion, neither layer 54 nor layer 44 need be used and layer 52 is a metal salt of the anion of choice, the metal being that of layer 50.

The salt of layer 54 will generally be a water soluble salt having a cation selected from ammonium, alkali metals and alkaline earth metals, since these are the ions most usually assayed using such electrodes, and as an anion a halogen or sulfur depending upon the composition of the metal salt layer. Conductive metal salts of these anions are commonly insoluble.

Appropriate solvents for the polymeric binder and ionic salt will depend largely on the nature of the polymer and the salt. Generally, polar solvents suitable for dissolving the salt and polymer are satisfactory. Water is a preferred solvent.

Considering now the ion-selective membrane 44, FIG. 4, such a layer comprises an ion carrier commonly called an ionophore, a carrier solvent and a binder. Binders for use in the ion-selective membrane include any of the hydrophobic natural or synthetic polymers capable of forming thin films of sufficient permeability to permit, in combination with the ion carrier and carrier solvent(s), apparent ion mobility thereacross. Specifically, polyvinyl chloride, polyurethanes (particularly aromatic polyurethanes), polyvinyl chloride, polyvinylidene chloride, polyvinyl butyral, polyvinyl formal, polyvinyl alcohol, polyvinylacetate, silicone elastomers, cellulose esters, polycarbonates, and mixtures and copolymers of such materials have been found useful. Films of such materials which include the ionophores and carrier solvents may be prepared using conventional film coating or casting techniques, and may be formed either by coating and film formation directly over the internal reference electrode or over an interlayer, or by separate formation and lamination thereto.

The ion carrier used in the ion-selective membrane is generally a substance capable of selectively associating or binding to itself a desired specific alkali metal, alkaline earth, ammonium or other ion.

The selectivity of the electrode for a particular ion is due to the chemical nature of the ion carrier and, thus, the use of different chemical components as the uncharged ion carrier provides different membranes for use in ion-selective electrodes specific to different ions. Exemplary carriers are published, for example, in the aforesaid Genshaw patent, as are certain requirements and examples of the carrier solvents.

Other useful examples of construction of the reference elements 46 can be found in the aforesaid Genshaw patent. The thicknesses of the layers as well as the concentration of the various ingredients are known design criteria within the skill of the art, as is typified by said Genshaw patent.

One or both of the ISE's used in the differential mode of measurement can be constructed so as to have as reference electrode 46, a dry conductive layer and at least one layer coated thereover which contains a redox couple compatible with the dry conductive layer to form a redox electrode. As disclosed in the aforesaid Battaglia application, such redox electrodes can comprise a conductive metal layer dipped into a solution containing two different oxidation states of a chemical species. An example of such an electrode comprises a platinum wire dipped into a solution containing ferrous and ferric ions. Redox elements of this type can also be prepared in a "solid-state" format to provide the internal reference half-cell of the composite ion-selective electrodes. Thus, the redox element preferably comprises: (a) a solid, electrically conductive layer in contact with (b) a redox couple.

The inert conductive layer of the reference electrode can comprise any suitable electrically conductive material or conductor (as this term is conventionally understood in the art) whose composition is such that it does not interact with the redox composition except in the desired and controlled electrochemical fashion required for operation of the electrode. Inert conductors such as carbon, platinum, gold and nickel can be used. The redox couples, as alluded to above, comprise pairs of the same chemical species (usually ions) in differing oxidation states.

Overlying the redox couple layer is an ion-selective membrane, constructed in the manner described above for the internal reference electrode.

The electrodes are mounted with the uppermost layers, i.e., layers 50 or 44, in contact with the bottom wall of groove 32, FIG. 3, by any suitable means such as adhesive, heat-staking, and the like. Preferably, the electrodes are completely fixed in place relative to the frame and to groove 32, to prevent errors caused by mechanical displacement of the electrodes.

The drops 100 and 102 in FIG. 4 are schematically illustrated as having cylindrical sides immediately adjacent the electrodes, which merely represents the manner in which they are confined by the access apertures, not shown in this view. The electrical circuit is, of course, completed by transport means 60 shown in phantom.

It is contemplated that an equivalent structure for certain ions is one in which paired electrodes are manufactured together, i.e., the top three layers 44, 54, and 52 are connected to form a continuous single electrode separated, however, at the silver layer 50. This is possible because of the inherent resistivity in the integral connection of the layers.

In addition to the electrodes described above for use in a differential measurement of potentials, device 20 can be used to measure direct potentials. In such a case multilayered, one of the electrodes must be an external reference electrodes not affected by changes in ion concentration in the test drop. Otherwise, the embodiment is identical to that described above, even as to the use of two drops of solution. However, it will be appreciated that in such an absolute mode of measurement, both drops 100 and 102 can be identical, i.e., taken from the same test sample. The external reference electrode, for example, electrode 42, can be multilayered such as would be obtained using a conventional silver/silver halide external reference electrode or a redox electrode as described above but without the ion-permeable membrane.

THE CAPILLARY BRIDGE OR TRANSPORT MEANS

As best shown in FIG. 2, the capillary bridge 60 is a means of transporting or promoting ionic migration between the electrodes. A preferred embodiment comprises such transport means positioned to contact the liquid solutions which, as noted, are preferably drops when the are applied to the apparatus. The element can be a variety of compositions and in a variety of forms. As shown in FIG. 1, the element is preferably a flat strip, the ends 68 of which overlap the locations A and B to which the drops of liquid are applied. Of necessity, the strip also overlies or is adjacent the electrodes 40 and 42. Optionally, the strip can be spaced away from the electrodes by a portion of the mounting frame 22, not shown.

When in strip form, the bridge 60 preferably comprises a support layer 70. To promote ionic migration along a continuous path between locations A and B, a porous layer 72 is coated or otherwise applied to the support. Thus, a preferred form of the transport element is a portion of a conventional thin-layer chromatographic sheet which can comprise, for example, a poly(ethylene terephthalate) film as the support and a porous layer coated thereover comprising a binder, a thickener, and a substance such as polycarbonate or polyamide mixed with atomized silica or glass powder. A highly preferred example of such a porous layer is polyamide, polycarbonate, or titanium dioxide chromatographic strips manufactured by Eastman Kodak.

It has been found that two features are desirable concerning the interface between the liquids and the electrodes. First, the interfacial area preferably remains substantially the same during the test reading. Second, because of the agitation generated by automatic handling equipment, means are provided to restrain each drop from contacting the edges of the membrane of the electrode while in fluid contact with a portion of the drop contacting the lower layers, such as would short out the electrode. To insure an appropriate interface of the liquid with, and ionic access to, the electrodes, at least the support layer 70 has, at the opposed ends 68, apertures 74. As shown, the layer 72 is also apertured. "Ionic access" as used herein means either direct contact of the liquid, preferably in drop form, to the electrode, or indirect contact as is achieved by migration through an ion-porous layer.

To restrain contact of the liquid with the edges of the operative layers of the electrodes, the device is designed to restrain flow of each drop under the bridge 60 and to the adjacent side of the electrode as would cause a short across any of the layers 48 through 52. One means for doing this is adhesive 76 applied at least around the apertures 74 to adhere bridge 60 to the electrode. Typical of such adhesives are acrylic latex adhesives. Alternatively, if bridge 60 is coated or otherwise applied to the electrodes by a step which seals the support layer 70 at apertures 74 to the exterior surface of the electrode, then flow of liquid beyond the access apertures is prevented and shorting is avoided.

The manner in which bridge 60 functions is to permit solvent and particularly ionic migration through layer 72 from one drop to the other, until they contact at a thin junction interface designated as 78, FIG. 1. Thus, the drops actually spread out into layer 72 from points A and B. For this reason, the drops need not be located precisely above apertures 74. It has been found that the construction of bridge 60 as described above is especially useful in providing a stable junction 78.

To further minimize liquid junction potentials that can be created at junction 78, layer 72 can be imbibed with hygroscopic gel saturated with a salt having ions of equal transference. Highly preferred gels include agar-agar, deionized gelatin and polyacrylamides, whereas suitable salts include lithium trichoroacetate, as well as $KNO_3$ and $NH_4NO_3$. The particular salt selected will depend on the ISE of choice. A useful formulation for such a gel can be, e.g., 3 g. of lithium trichloroacetate and 0.2 g. agar-agar dissolved in 5 ml of boiling water. Such saturated gels have such a high concentration of ions that the junction potential which might otherwise be created is lost in the ion flow created by the gel. Such dominating ion flow is only negligibly affected by the junction potential created by the two different concentrations of the drops. Thus the saturated bridge in effect creates two equal junction potentials at its interface with the liquid drops, which are of opposite sign so as to cancel out. It has been found, for example, that an interfacial potential without the use of such gel, read on electrometer 80 as 53 to 56 millivolts for a test sample which would have a predicted Nernstian potential of 59mV, is brought closer to the predicted value when the gel is pre-imbibed into bridge 60. When the saturated gel is used, electrometer readings are effective even before the liquid of the two drops deposited on the electrodes make contact within the bridge.

Still other suitable materials which can be coated as layer 72 include titanium dioxide dispersed in suitable binder such as polyvinyl alcohol or cellulose acetate, as well as so-called microporous filter membranes of "blush polymer" materials made, for example, from cellulose esters, and containing pores of microscopic size. Among the materials of this latter type which are commercially available are filter materials sold under the trademark Millipore by the Millipore Corporation and those sold under the trademark Metricel by the Gelman Instrument Company. Other well-known "blush polymer" layers can be formed by dissolving a suitable polymer (e.g., cellulose acetate) in a mixture of two liquids, one of which is a good solvent for the polymer and the other of which is of higher boiling point and either a nonsolvent or at most a poor solvent for the polymer, coating the polymer solution on the support and drying. Since the good solvent will evaporate more readily because of its lower boiling point, the coating becomes enriched in the poor solvent or nonsolvent as evaporation proceeds and, in consequence, the polymer precipitates out in the layer of fine particles and forms an adherent porous layer.

Although the embodiment of FIG. 1 illustrates the test and/or reference drops being deposited immediately at or aligned with the access apertures 74 leading to the electrodes, it will be appreciated that suitable construction of the capillary bridge will permit the drops to be deposited out of alignment. Diffusion through the bridge in such a case brings the liquids into contact with their respective electrodes.

THE ELECTROMETER

Turning now to FIG. 5, electrometer 80 preferably is a low-drift, high-input impedance potentiometer having an impedance which exceeds that of the electrodes' impedance. Thus, it is preferred that capacitance pickup be minimized. A typical circuit providing these features is illustrated in FIG. 5.

The electrometer preferably comprises input 83, preferably a shielded cable, connected to an operational amplifier 85 used as a voltage follower. A relay 86 can be used to short out the amplifier so that a variable resistor 87 can be adjusted to zero the amplifier. Optionally, leads 88 connect the amplifier to a conventional computer and power supply, not shown, whereby the zero offset of the electrometer, if any, can be automatically stored and corrected.

Any amplifier useful as a voltage follower can be used, provided its impedance is considerably in excess of the internal impedance of the electrodes. By controlling the humidity of the electrodes, as discussed hereinafter, it has been found that the latter impedance is on the order of 1 megohm or less. Thus, the input impedance should be between about $10^{10}$ and $10^{14}$ ohms. Preferably, the amplifier also has a small bias current, to minimize the voltage drop across the internal impedance, which represents a built-in error. Preferred values of the bias current are 15 to 20 picoamps or less.

Typical operational amplifiers which meet the above criteria are the Burr-Brown Series 3521 FET input amplifiers manufactured by Burr-Brown Research Corporation.

Alternatively, a digital readout, not shown, can be positioned in series between one of the probes and the electrometer and, further, the potentials can be compared automatically by a conventional microcomputer and a readout of the difference displayed.

Figure 6:
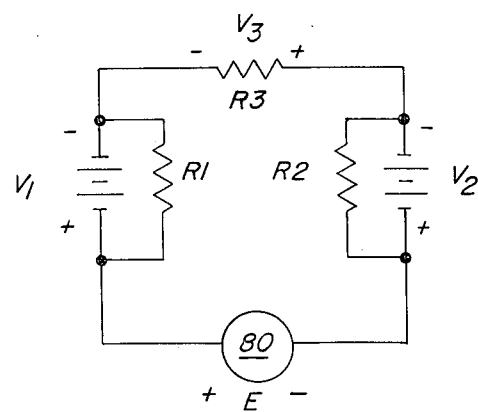
FIG. 6 is a schematic circuit representing the electrical equivalents of the circuit shown in FIGS. 1 and 4.

FIGS. 6 illustrates the complete electrical circuit formed when the drops of solution have contacted the electrodes and each other via the transport element, and when the electrometer 80 has contacted the electrodes as shown in FIG. 1. That is, one of the electrodes will develop a potential $V_1$ and the other a potential $V_2$ at the interface of the electrode with its drop. The respective values of these potentials are governed by the concentration of the ion that permeates through membrane 44. $V_3$ must be kept small as it detracts from the reading, that is, $E = V_1 - V_2 + V_3$, $V_1 - V_2$ representing the desired value for conversion to activity per the Nernst equation. As noted above, $R_3$, and therefore $V_3$, is kept small by minimizing the junction potential created at the interface in the transport element 60 between the two drops.

$R_1$ and $R_2$ are the internal impedance of each electrode and, in the differential mode, they are the same as the electrodes are identical.

OPERATION

Electrodes of the type described above usually have a potential which experiences drift. Such drift can actually be calibrated. Using such "calibrated drift," ion concentration is readily, reproducibly, accurately and precisely determinable. Alternatively, drift variations can be compensated for by using a differential measurement which compares the ion activity of the unknown sample with that of a similar sample of known ion concentration (i.e., a calibrator or standard) simultaneously spotted on an identical electrode. When the electrodes are used in the differential mode, as can be done in all the embodiments shown in the figures except that shown in FIGS. 14 and 15, since the paired electrodes are identical, their curves are identical and the trough characteristics cancel out.

Operation of device 20 in the differential mode proceeds by spotting a drop 102 of the reference solution on either point A or B and a drop 100 of the test solution on the other point, FIG. 4. Probes 84 are either simultaneously or subsequently moved into contact with layer 50 of the electrodes, and the potentials are read on electrometer 80 or digital display, if used. The frame mount is then removed from contact with the electrometer 80 and disposed of, and a new frame with its electrodes is positioned to receive the drops of liquid and to contact the electrometer. It will be appreciated that, because of the simplicity, approximately planar configuration, and size of frame mount 22, the device readily lends itself to automated handling wherein the frame is moved through a plurality of stations, one of which comprises a pair of probe arms which are thrust into contact with layers 50 when the potentials are to be read.

Any automated handling devices can e used to move the completed device 20 between processing stations. For example, indexing means for sliding the device along a suitable track, preferably in a controlled environment, can be used. As such devices are conventional and within the skill of the art, no further description of them is necessary.

It has been found that a device constructed as described above, with suitable temperature controls and electrical isolation, is capable of measuring the potentials created by the ion of choice to the following accuracy:

± 0.25 mV for $Na^+$;
± 0.4 mV for $Cl^-$;
± 0.6 mV for $K^+$.

Using the conventional Nernstain plot of $\Delta E$ (potential) vs. log A (activity), the activity of the ion is readily ascertainable from these readings. By similarly measuring the activity of the ions in a known solution having a known concentration, the concentration of the test solution is thus determined.

MODIFICATIONS

In some tests, such as in determining activity of $CO_2$, it is preferred that the drops be isolated from the atmosphere to prevent $CO_2$ equilibration between the ambient atmosphere and the test solution. In still other tests, it is preferred that evaporation of solvent be minimized. In those instances, frame 22 can be modified to include, as shown in FIG. 7, a cover portion 90 which is attached by flexible hinge 92 to the frame 22. Cover portion 90 has an inner surface 94 which is cut away to provide a dome which fits over the groove 34 to seal the drops from contamination or evaporation, as shown by the dashed lines. Or, alternatively, portion 90 can extend to cover the entire frame 22.

Figure 8:
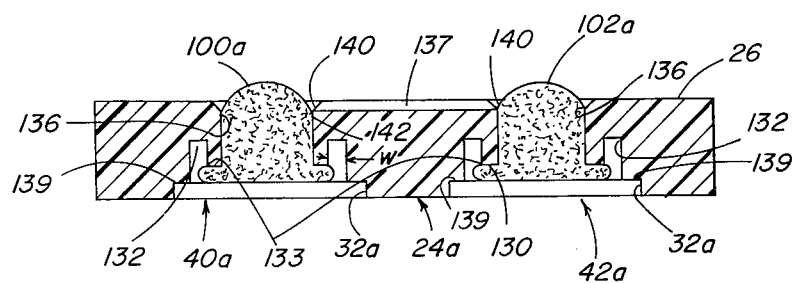
FIG. 8 is a sectional view similar to FIG. 2 but illustrating an alternate embodiment.
Figure 9:
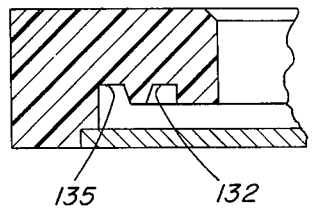
FIG. 9 is a fragmentary view similar to FIG. 8 but illustrating another modification.
Figure 10:
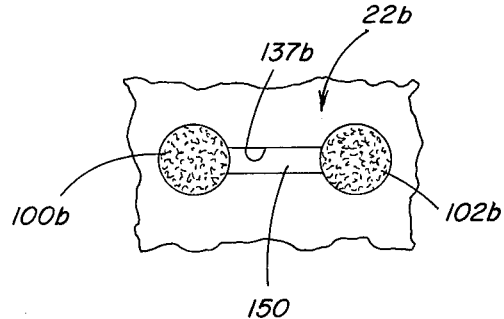
FIG. 10 is a fragmentary schematic plan view of a bridge that can be constructed utilizing the features shown in FIG. 8.

FIGS. 8–10 illustrate alternate embodiments for the transport element. Parts similar to those previously described bear the same reference numeral, to which the distinguishing suffixes "a", "b" and "c" have been appended. Thus, in FIGS. 8 and 9, there is shown a modification of the transport element such that it extends only between apertures 136 of frame 22a, in the form of groove 137, and is greatly reduced in dimension so as not to exceed about 10 mm. as the maximum dimension transverse to be flow path. To prevent short-circuiting of the electrodes by contact of the drops 100a or 102a with the edges of the operative layers of the electrode, the grooves 32a containing the electrodes 40a and 42a have been modified to form flow-restraining means. Specifically, the frame is constructed with a platform 130 spaced away from the electrodes, such as a distance of 0.25 mm, for example, and apertures 136 connect the grooves 32a to surface 26a. These apertures are further undercut to form annular grooves or rings 132 therearound. The effect is to cause the drops 100a and 102a of liquid to sit on the platform 130, due to surface tension effects, as shown by their annular portions. Without rings 132, the tendency of either drop would be to flow along its electrode until it contacts the side surface 32a of the electrodes where the drop can short-circuit the effect of top layers 48, 52 and 54. To provide an effective restraint to meniscus flow, it is preferable that grooves 132 have a minimum width "w",FIG. 8, of at least about 0.025 cm., and that edge 133 defined by the intersection of platform 130 and groove 132 have a radius of curvature no greater than about 0.04 cm. Alternatively, yet another annular groove 135 surrounded by and concentric with each groove 132, FIG. 9 can be formed in the event only one such groove is an inadequate restraint as may occur, for example, if the electrodes are warped out of a planar configuration. In either construction, a typical surface area for the platform 130 for drop volumes of about 10 $\mu$ l is about 20.0 sq. mm., as typically is defined by an inner diameter, of aperture 136, of about 2.0 mm., and by an outer diameter, for edge 133, of about 5.0 mm.

An additional optional feature to prevent the liquid from contacting the edges of the electrodes in the application of adhesive along the side of the top layer of the electrodes at 139, where the top layer of the electrodes contacts groove 32a.

To prevent spreading of the drop across surface 26a of the frame, apertures 136 are reamed at 140 to create a sloped surface intersecting apertures 136 at a liquid-confining edge 142.

The groove 137 can be used without any porous layer or additional material, provided it is coated with a surfactant capable of promoting ionic migration, such as "Triton X-100," an octylphenoxy polyethoxy ethanol produced by Rohm & Haas, or "OLIN 10G," a nonylphenoxy polyglycerol produced by Olin-Mathieson, if the plastic of the frame is hydrophobic. The drops will then flow together by reason of capillary effect to create a junction. However, streaming potentials across such junctions can be minimized by securing within groove 137 a transport element including the strip of bridge 60 described above, with or without the support layer 70. Alternatively, a fibrous material can be used which is sufficiently porous and hydrophilic as to promote ionic migration therethrough. Hydrophilicity can be improved by the addition of the aforesaid surfactants. Typical fibers which can be used include polyesters such as poly(ethylene terephthalate); spun yarn such as nylon, e.g., nylon 6, and rayon; Verel (a copolymer of acrylonitrile and vinylidene chloride) and cotton and silk threads such as Brook's basting thread manufactured by Coats & Clark, Inc. and "Kresge 60"manufactured by S.S. Kresge Company. The fibrous material can be anchored to groove 137 by heat, pressure or an adhesive that is nonreactive with the liquids to be spotted. Preferably, when the fibrous material is used, the groove 137 is not precoated with a surfactant but remains highly hydrophobic, to confine the liquid to the fiber.

As shown in FIG. 10, yet another alternative part of the transport means or salt bridge is the salt-saturated hydroscopic gel 150 described in connection with the embodiment of FIG. 1, coated or deposited within groove 137b of the type shown also in FIG. 8, and extending the full distance between drops 100b and 102b, on frame 22b. It will be appreciated that, in this case, the drop ions and/or solvents do not migrate half the length of the passageway or groove 137b to form a junction. Instead, the drops migrate into and out of the gel. The potential of the junction is minimized as described before by the swamping effect of the ions of the gel, whereby a reading closet to the theoretical Nerstian value is achieved.

Figure 11:
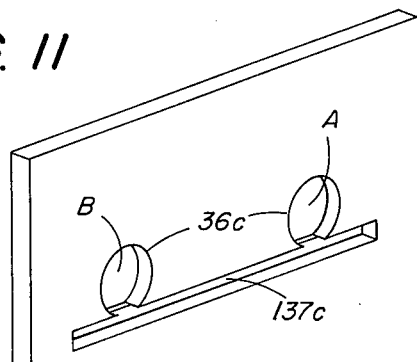
FIG. 11 is an isometric view similar to FIG. 1 which illustrates yet another embodiment.

In FIG. 11, a structure similar to that shown in FIG. 8 is illustrated, except that the groove 137c has been displaced out of the centerlines of apertures 36c to a position in which the groove is tangent but still adjacent the apertures. When the drops are placed on frame 22c at points A and B to contact electrodes 40c and 42c, the transport means is still in contact with the drops, promoting ionic migration. As in the case of the embodiments of FIG. 8, any or none of the transport elements described heretofore can be applied to groove 137c.

Figure 12:
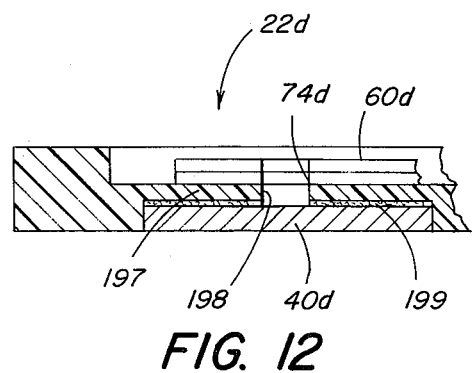
FIG. 12 is a fragmentary sectional view similar to FIG. 2 but illustrating yet another alternate embodiment.

FIG. 12 illustrates an alternate form of the embodiment shown in FIG. 2, wherein frame 22d is modified so as to have a portion 197 extending between the ISE 40d and the bridge 60d, aperture 198 of portion 197 being generally aligned with aperture 74d of the bridge. An adhesive ring 199 preferably surrounds aperture 198 adjacent the electrode to prevent the liquid drop from moving to the edges of the electrode by capillary action such as would cause shorting of the electrode.

Figure 13:
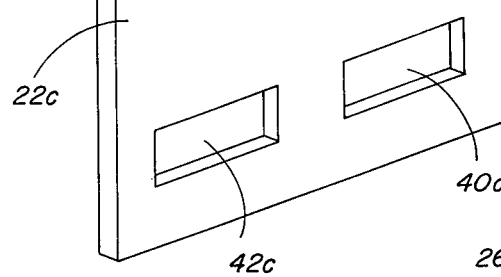
FIG. 13 is an isometric view of a mounting frame and electrodes representing still another embodiment.
Figure 14:
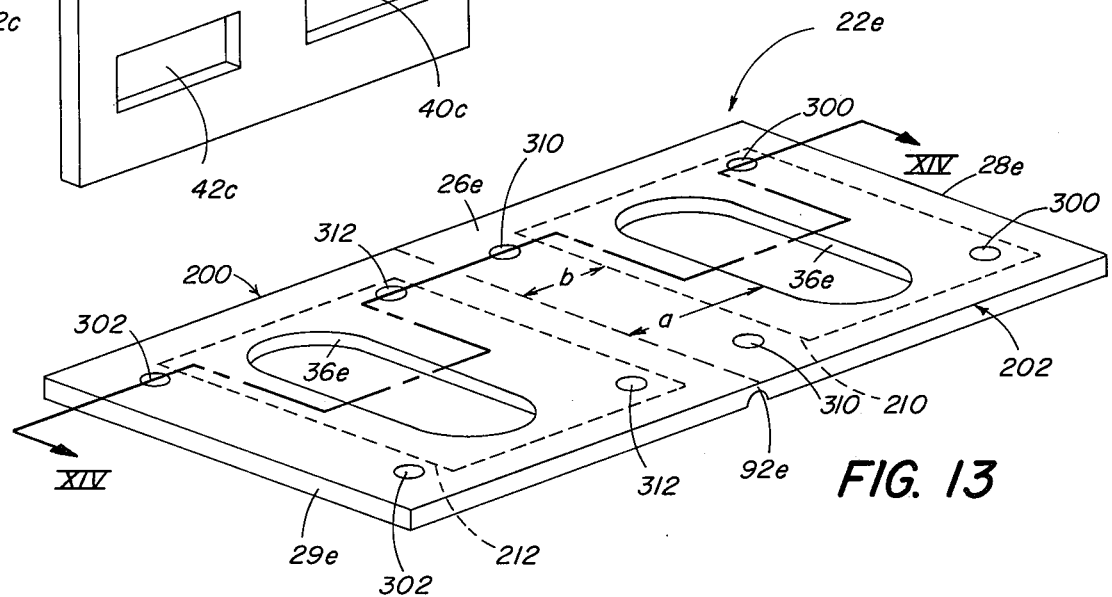
FIG. 14 is a sectional view taken generally along the plane XV—XV of FIG. 13, after the two portions are folded together, illustrating the use of the apparatus of FIG. 13.

Turning now to FIGS. 13 and 14, there is illustrated yet another embodiment designed for use preferably in the absolute mode. Parts similar to those previously described bear the same reference numeral to which the distinguishing suffix "e" is appended. In this embodiment, apparatus 20e comprises a frame 22e having two halves 200 and 202 connected by a hinge portion 92e located along the mid-plane of the element, such that one half acts as a cover for the other when the frame is closed for a test as shown in FIG. 14. Each half in turn has a groove or cavity 32e formed in its interior in which is confined an ISE 40e or 42e, one of which must be an external general reference electrode such as is formed using the redox couple element described above. The other electrode is of the type having the metal-metal salt reference half-cell described above. Surface 26e also has two apertures 36e adjacent to and opening into each groove 32e. These apertures permit ionic access from the drop of test sample to the electrodes. The apertures 36e are generally equidistant (distance "a") from the hinge portion 92e to insure that they will be aligned as shown in FIG. 14. Grooves 32e, however, are offset such that the inside edge 210 of the groove 32e in half portion 202 is a distance "b" away from hinge portion 92e, while outside edge 212 of groove 32e in half 200 is the same distance away from edge 29e of the entire frame. Distance "b" is, of course, less than distance "a". By this construction, the probes 84e for electrometer 80e can contact the electrodes through the covering portion of the frame, simply by reason of the following additional access apertures: Paired apertures 300 and 302 are formed equidistant from edge 28e and edge 29e, respectively, the apertures 300 extending from surface 26e only into connection with groove 32e, and apertures 302 extending all the way through the frame in a nonconducting portion thereof from surface 24e to surface 26e. Paired apertures 310 and 312 are formed equidistant from hinge portion 92e, respectively, the apertures 310 extending all the way through the frame in a nonconducting portion thereof from surface 24e to surface 26e and apertures 312 extending only from surface 26e into connection with groove 32e. Thus, when halves 200 and 202 are folded together, apertures 300 and 302 become aligned, as do apertures 310 and 312, permitting one probe 84e, FIG. 14, to pass through apertures 302 and 300 into contact with electrode 40e, and the other probe 84e to pass through apertures 310 and 312 into contact with electrode 42e.

To permit ready insertion of the electrodes into interior grooves 32e, portions 320 and 322 can be cut out of halves 202 and 200, respectively, and reinserted and adhered as by adhesive after the electrodes are in place. The adhesive at portions 323 restrains the drop from flowing across the ion-selective membrane or otherwise coming into shorting contact with the underlying operative layers.

It will be appreciated that, in this embodiment, ionic migration between the electrodes is achieved by means of the alignment of the apertures when the frame is folded about hinge portion 92e, so that the single drop 100e contacts both electrodes. By this contruction, the necessity for two drops and the use of a salt bridge is eliminated.

EXAMPLES

The following examples are illustrative only, and are not considered to be exhaustive. The first two examples are taken from the aforesaid Battaglia application and are incorporated herein to demonstrate the manufacture of an electrode useful in the device of this invention.

EXAMPLE 1

Reference half-cell

A sample of vacuum-deposited metallic silver on polyethylene terephthalate support (10 mg. Ag/dm.$^2$)

was prepared. A portion of this sample was treated for 5 min. in the following solution:

glacial acetic acid: 0.45 ml.
sodium hydroxide: 0.20 g.
potassium ferricyanide: 0.80 g.
potassium chloride: 2.50 g.
distilled water to 1 liter.

The sample was then washed for 5 min. in running distilled water, dipped in a 1% solution of deionized gelatin at 40° C. for 1 min., and dried.

Visual inspection revealed that partial conversion to silver chloride had occurred, leaving a contiguous layer of metallic silver adjacent the support. The coverage was 7.6 g./m.$^2$ total silver with 15% conversion to AgCl. A narrow strip along one edge was dipped briefly in a thiosulfate bath to uncover the silver layer for purposes of making electrical contact.

The AgCl layer was then coated with a 5% polyvinyl alcohol (PVA) — M KCl solution (1.5 g. KCl, 5.0 g. PVA/m.$^2$). After the PVA layer was dried in a drying chamber at about 85° F. for a period of 6 hr., a precast ion-selective membrane comprising 0.50 g./m.$^2$ of valinomycin (VAL), 40.4 g./m.$^2$ of polyvinyl chloride (PVC) and 100.2 g/m.$^2$ of bromophenyl phenyl ether as carrier solvent (BPPE) was manually laminated on top of the film coating.

The resulting integral electrode, represented as Ag-/AgCl/PVA-KCl/ion-selective membrane was tested by:

1. connecting the silver-silver chloride film to the high impedance input of an electrometer; and
2. suspending a drop (25 - 50 μl) of the KCl solution to be measured from the tip of a saturated NaNO$_3$ salt bridge which is connected to an external reference electrode (Hg/HgCl$_2$) which is connected to the reference input of the electrometer, and contacting the drop to the surface of the integral electrode.

The complete potentiometric cell is thus represented by Hg/HgCl$_2$/KCl (XM) test/ion-selective membrane, PVA-KCl/AgCl/Ag.

A linear semilogarithmic response to potassium ion was observed with a slope of 57 Mr/decade over the range pK+1 to 4.

EXAMPLE 2

A redox reference electrode having a double-layer structure was prepared by coating poly(ethylene terephthalate) film support with a conductive layer comprising deionized gelatin (9.7 g./m.$^2$), particulate carbon (15.5 g./m.$^2$) and Triton X-100 (0.28 g./m.$^2$) and a redox layer as described above comprising dionized gelatin (4.85 g./m.$^2$) as a binder, potassium ferricyanide (5.4 meq./m.$^2$) and potassium ferrocyanide (5.4 meq./m.$^2$). The resulting reference electrode was manually laminated to a precast ion-selective membrane comprising valinomycin (VAL) (0.49 g./m.$^2$), bis(2-ethylhexyl)-phthalate (BEHP) (14.5 g./m.$^2$) and polyvinyl chloride (PVC) (9.2 g./m.$^2$).

The resulting composite ion-selective electrode was tested in the following cell:

Table 1

| 0.15M NaCl CE | // | 50 λ drop of 0.15M NaCl containing 10$^{-1}$ to 10$^{-4}$ KCl | // | ion-selective electrode |

| Potassium Ion Response Fe$^{+2}$/Fe$^{+3}$ Internal Reference | |
|---|---|
| KCl M | 2 Minutes (mv) |
| 10$^{-4}$ | −59.0 |
| 10$^{-3}$ | −3.7 |
| 10$^{-2}$ | +54.4 |
| 10$^{-1}$ | +108.2 |

The emf at 2 min. showed a linear semilogarithmic dependence on potassium ion concentration with a slope of 57 mv/decade. The potential drifted with time after spotting the element with 50λ of test solution. The magnitude of the drift was about 0.1 mv/min. between 2 and 10 min.

EXAMPLE 3

A device of the type shown in FIGS. 1 and 2 was manufactured using identical, parallelly positioned chloride ISE's prepared similarly to the description in the first three paragraphs of Example 1. The ISE's, 22 mm. by 8 mm., were inserted into the frame and a capillary bridge was formed by cutting a "K511V (6067)" polycarbonate chromatographic sheet manufactured by Eastman Kodak into a strip 15 mm. by 8 mm. Two holes were punched into the strip to align with the electrodes. Double-sided adhesive tape comprising "Scotch" brand double-coated adhesive No. 665 manufactured by 3M was applied to the base of the chromatographic strip and to the electrodes, securing the strip to the electrodes.

Two 10 μl drops of serum having identical Cl concentrations were simultaneously applied to the holes in the bridge. After a 2 minute delay during which the drops made contact within the bridge and to the electrodes, the mean potential of 9 measurements made on the aforedescribed electrometer was 0.15 mV with a standard deviation of ±0.15 mV and an average drift rate of 0.039 mV/minute over a 5 minute period.

EXAMPLE 4

A device was manufactured as in Example 3, except that potassium ISE's were used, manufactured as described in Example 1. The test drops were "Versatol" solutions of differing K+ concentrations, namely, 3.1 mM and 5.0 mM. "Versatol" is an artificially prepared calibrator manufactured by General Diagnostics, a division of Warner-Lambert Co., and contained in addition to the ion of choice about 7 weight percent total albumin and protein. The electrometer readings taken over a 5 minute period from the deposition of the drops on the device are set forth in the following table:

| Test Minute | Mean Reading | Standard Deviation |
|---|---|---|
| 1 | 12.13 mV | ±0.35 mV |
| 2 | 11.91 | 0.37 |
| 3 | 11.66 | 0.30 |
| 4 | 11.73 | 0.30 |
| 5 | 11.79 | 0.33 |

EXAMPLES 5 and 6

In each example, a device of the type shown in FIG. 9 was manufactured by inserting chloride ISE's of the type used in Example 3, into a polystyrene frame. The capillary groove comprising the bridge or transport means was coated with a 2% solution of "Olin 10 G", a nonionic nonylphenoxy polyglycerol surfactant manufactured by Olin Mathieson, and air dried at 50° C.

In Example 5, a drop from each of two saline solutions containing 100 mM and 150 mM Cl, respectively, was deposited on one of the apertures in the frame between which the capillary groove extends. The potential measured by the electrometer was within 2% of the assayed test concentration. In Example 6, a drop from each of the 100 mM concentrated saline solution of Example 5, and from a Versatol solution containing 104 mM Cl⁻, was deposited on one of the apertures. The potential measured by the electrometer was within 6% of the assayed chloride concentration.

EXAMPLE 7

A device of the type shown in FIG. 11 was prepared by depositing on a fiber in the capillary groove, a saturated gel in melted form, comprising 4 M $NH_4NO_3$ (saturated) in gelatin. Upon cooling, the gel solidified. The ISE's were the same as in Examples 5 and 6. When two drops frm two different sodium chloride solutions were deposited at opposite ends of the bridge, in the apertures leading to the ISE's, after 2 minutes a mean reading of $-27.18$ mV was achieved, and after 4 minutes a mean reading of $-26.74$ mV resulted. This compared with a theoretical expected value of about $-29$ mV. When the test was repeated but without the saturated salt gel, the mean readings were only $-20.30$ mV, respectively. Thus, the gel was effective in eliminate about 7 mV of the junction potential.

EXAMPLES 8 and 9

In each example, a device of the type shown in FIG. 11 was manufactured, the capillary bridge being formed by staking a "Kodel-2" thread, a fiber manufactured by Eastman Kodak, to the groove running tangent to the ion access apertures. The ISE's were again chloride ISE's similar to those used in the previous example.

In Example 8, two drops were taken from the same "Versatol" solution as in Example 7, and the mean value registered by the electrometer in six tests was $-0.25$ mV with a standard deviation of $\pm 0.05$ mV. In Example 9, a drop from each of a "Versatol" solution containing 101.4 mM Cl⁻ and from a "Versatol-A" solution containing 91 mM Cl⁻, was deposited on the ion access apertures. The drops wetted the capillary bridge, and after 2 minutes the mean value of 9 tests registered on the electrometer was $-2.68$ mV with a standard deviation of $\pm 0.18$ mV.

The invention has been described in detail with particular reference to certain preferred embodiments thereof, but it will be understood that variations and modifications can be effected within the spirit and scope of the invention.

What is claimed is:

1. A device useful for determining the activity of ions in a liquid solution, comprising:
   a frame capable of being processed by automatic handling devices,
   two solid electrodes mounted with respect to said frame, each comprising a first operative layer coated over at least one other operative layer, said layers terminating at edges,
   means for providing ionic flow between said electrodes upon application of one or more liquid drops, and
   at each electrode, anti-shorting means for restraining the liquid from simultaneously contacting the edges of both of said layers.

2. The device as defined in claim 1 wherein said flow-providing means includes a frame to which said electrodes are secured in a spaced-apart electrically isolated relationship.

3. The device as defined in claim 2 wherein said restraining means includes a platform adjacent and spaced away from each of said electrodes, and an annular groove separating said platform from the rest of said frame, said groove having a geometry and dimensions which are sufficient to confine the drop to that portion of said electrode which is adjacent said platform.

4. The device as defined in claim 2 wherein said frame and said electrodes are generally planar.

5. The device as defined in claim 1 wherein said flow-providing means includes transport means for promoting migration of ions away from the drops in liquid contact with each of said electrodes.

6. The device as defined in claim 5 wherein said transport means includes a porous layer extending between said electrodes.

7. The device as defined in claim 6 wherein said porous layer comprises a binder, a thickener and a polymer selected from a polycarbonate or a polyamide.

8. The device a defined in claim 5 wherein said transport means includes a thin-layer chromatographic strip having a porous layer coated over a support.

9. The device as defined in claim 5 wherein said flow-providing means includes a frame to which said electrodes are secured and a passageway in said frame extending between said electrodes.

10. The device as defined in claim 9, and further including a transport element disposed in said passageway.

11. The device as defined in claim 10 wherein said element comprises a support and a porous layer coated over the support.

12. The device as defined in claim 10 wherein said element comprises a fibrous material in said passageway.

13. The device as defined in claim 5 wherein one of the electrodes is a reference electrode and the other of said electrodes is an ion-selective electrode.

14. The device as defined in claim 1 wherein said electrodes are the same and are ion-selective electrodes, said first layers being selectively permeable to a specific ion.

15. The device as defined in claim 14 wherein said flow-providing means includes transport means for promoting migration of ions between two drops of different ionic strength, each in contact with one of said electrodes, said electrodes being sufficiently close together as to permit said migration until the solutions from said drops are in contact to form an ionic junction.

16. The device as defined in claim 15, and further including means for minimizing the potential at the ionic junction.

17. The device as defined in claim 16 wherein said minimizing means includes a hydroscopic gel saturated with an ionically conductive salt.

18. The device as defined in claim 17 wherein said transport means includes a porous layer extending between said electrodes, said gel being imbibed in said layer.

19. The device as defined in claim 15 wherein said transport means includes a porous layer extending between said electrodes.

20. The device as defined in claim 15 wherein said transport means includes a passageway in said frame extending between said electrodes.

21. The device as defined in claim 20, and further including a transport element disposed in said passageway.

22. The device as defined in claim 21 wherein said element comprises a fibrous material in said passageway.

23. The device as defined in claim 1 wherein said frame for mounting said electrodes includes:
   a cavity, said electrodes being fixedly mounted within said cavity, and
   at least one aperture adjacent and connected to said cavity and to one surface of said frame to permit access to said cavity.

24. The device as defined in claim 23 wherein said reference electrode includes, as operative layers:
   a. a solid reference element and,
   b. in intimate contact with the reference element, a hydrophobic ion-permeable membrane.

25. The device as defined in claim 24 wherein said reference element includes a metal-metal salt reference half-cell and a dry hydrophilic electrolyte solution in conducting contact with said half-cell.

26. The device as defined in claim 24 wherein said reference element includes a dry conductive layer and at least one layer coated thereover containing a redox couple compatible with said conductive layer.

27. A device useful for determining the activity of ions in a liquid solution, comprising:
   a frame capable of being processed by automatic handling devices,
   two solid electrodes secured to said frame, each comprising a first operative layer coated over at least one other operative layer, said layers terminating at edges, one of said electrodes being a reference electrode and the other being an ion-selective electrode,
   means for providing ionic flow between said electrodes upon application of one or more liquid drops, and
   at each electrode, anti-shorting means for restraining the liquid from simultaneously contacting the edges of both of said layers.

28. The device as defined in claim 27 wherein said flow-providing means includes a frame to which said electrodes are secured in a spaced-apart electrically isolated relationship.

29. The device as defined in claim 28 wherein said restraining means includes a platform adjacent and spaced away from each of said electrodes, and an annular groove separating said platform from the rest of said frame, said groove having a geometry and dimensions which are sufficient to confine the drop to that portion of said electrode which is adjacent said platform.

30. The device as defined in claim 28 wherein said frame has:
   a pair of cavities, said electrodes being fixedly mounted within said cavities, and
   at least one aperture adjacent and connected to each of said cavities and to one surface of said frame to permit access to said cavities.

31. The device as defined in claim 30 wherein said flow-providing means includes a hinge positioned between said apertures such that, when said frame is folded about said hinge, said apertures are aligned and a single drop of solution can contact both electrodes.

32. The device as defined in claim 31 wherein said frame includes additional apertures extending from said one surface into either said cavities or all the way through an insulative portion of said frame, such that, when said frame is folded about said hinges, said additional apertures are aligned to permit a probe to extend through said portion of the frame into contact with one of said electrodes.

33. A device useful for determining the activity of ions in a liquid solution, comprising:
   two solid electrodes, each comprising a first operative layer coated over at least one other operative layer, said layers terminating at edges, one of said electrodes being a reference electrode and the other being an ionselective electrode,
   means for providing ionic flow between said electrodes upon application of one or more liquid drops,
   at each electrode, anti-shorting means for restraining the liquid from simultaneously contacting the edges of both of said layers and
   a frame to which said electrodes are secured in a spaced-apart electrically isolated relationship, said frame including at least one cavity in which said electrodes are mounted, and at least one aperture adjacent and connected to said cavity and to one surface of said frame to permit access to said cavity and hence to at least one of said electrodes.

* * * * *

UNITED STATES PATENT AND TRADEMARK OFFICE
CERTIFICATE OF CORRECTION

Page 1 of 2

PATENT NO. : 4,053,381
DATED : October 11, 1977
INVENTOR(S) : David P. Hamblen, Clyde P. Glover and Sang H. Kim It is certified that error appears in the above-identified patent and that said Letters Patent are hereby corrected as shown below:

Column 3, line 59 "ionselected" should read --ion-selective--.

Column 5, line 3 after "comprises" --a-- should be inserted.

Column 7, line 28 "concentration" should read --concentrations--.

Column 8, line 18 delete "multilayered,".

Column 8, line 19 "electrodes" should read --electrode--.

Column 9, line 38 "trichoroacetate" should read --trichloroacetate--.

Column 9, line 62 after "in" --a-- should be inserted.

Column 10, line 61 "FIGS." should read --FIG.--.

Column 11, line 46 delete "e" and insert --be--.

Column 11, lines 59-61

"$Na^+$
$Cl^-$
$K^+$ should read

--$Na^\oplus$
$Cl^\ominus$
$K^\oplus$--.

UNITED STATES PATENT AND TRADEMARK OFFICE
CERTIFICATE OF CORRECTION

PATENT NO. : 4,053,381

DATED : October 11, 1977

INVENTOR(S) : David P. Hamblen, Clyde P. Glover and Sang H. Kim

It is certified that error appears in the above-identified patent and that said Letters Patent are hereby corrected as shown below:

Column 13, line 36 after "Instead," insert --the ions of--.

Column 15, line 22 "(PVA)-M" should read --(PVA) - 0.2 $\underline{M}$ --.

Column 15, line 49 "Mr" should read --Mv--.

Column 16, line 38 "Cl" should read --$Cl^-$--.

Column 17, line 35 after "only" insert -- -20.56 mV and--.

Column 17, line 36 "eliminate" should read --eliminating--.

Signed and Sealed this

Twenty-eighth Day of March 1978

[SEAL]

Attest:

RUTH C. MASON
Attesting Officer

LUTRELLE F. PARKER
Acting Commissioner of Patents and Trademarks